United States Patent [19]

Elias

[11] 4,327,728
[45] May 4, 1982

[54] CATAMENIAL DEVICE WITH AN ABSORBENT LAYER HAVING ADMIXTURE OF DISCRETE SUPERABSORBENT AND INTROFYING PARTICLES

[75] Inventor: Robert T. Elias, Downers Grove, Ill.

[73] Assignee: Johnson & Johnson Baby Products Company, New Brunswick, N.J.

[21] Appl. No.: 153,709

[22] Filed: Jun. 4, 1980

Related U.S. Application Data

[63] Continuation-in-part of Ser. No. 954,152, Oct. 24, 1978, abandoned.

[51] Int. Cl.$^3$ .................... A61F 13/20; A61F 13/16
[52] U.S. Cl. .................... 128/285; 128/290 R
[58] Field of Search .................... 128/285, 284, 290 R

[56] References Cited

U.S. PATENT DOCUMENTS

| | | | |
|---|---|---|---|
| 3,121,427 | 2/1964 | Mosier | 128/284 |
| 3,900,378 | 8/1975 | Yen et al. | 128/285 X |
| 3,958,561 | 5/1976 | Bucalo | 128/285 X |
| 4,055,180 | 10/1977 | Karami | 128/287 |

*Primary Examiner*—P. Ives
*Attorney, Agent, or Firm*—Martha A. Michaels

[57] ABSTRACT

A catamenial device such as a tampon, a sanitary napkin or the like, is disclosed which includes an absorbent layer having at least one pocket containing a uniform admixture of discrete superabsorbent particles and discrete introfying particles.

23 Claims, 7 Drawing Figures

CATAMENIAL DEVICE WITH AN ABSORBENT LAYER HAVING ADMIXTURE OF DISCRETE SUPERABSORBENT AND INTROFYING PARTICLES

This application is a continuation-in-part application of copending application U.S. Ser. No. 954,152 filed Oct. 24, 1978 now abandoned.

BACKGROUND OF THE INVENTION

This invention relates to an improved catamenial device such as a tampon, sanitary napkin or the like. More particularly, this invention provides a superabsorbent batt or body component especially desirable for use in disposable absorbent products.

The most common absorbent material used in disposable products is a mass of cellulose fibers. Although the cellulose itself will absorb some liquid, causing the fibers to swell, most of the absorbed liquid is held in the capillary spaces among the fibers. The liquid within the cellulose fibers is difficult to remove, but the liquid held in between the fibers is removed readily by squeezing.

Much effort has been expended to find materials which will be more cost effective than cellulose fibers with respect to liquid absorbency and retention. Typical materials and various ways of incorporating them into absorbent products are disclosed in U.S. Pat. Nos. 3,344,789, 3,683,917, 3,783,872, 3,814,101, 3,815,601, 3,886,941, 3,890,974, 3,898,143, 3,900,378, 3,901,231, 3,901,236, 3,956,224, 3,957,605, 3,963,805, 4,058,124, 4,090,013, 4,103,062 and 4,105,033.

Some of the more promising materials are in the form of granules, beads, fibers, etc. which take liquid into their respective structures resulting in swelling and becoming like a gel. These materials are called superabsorbents. Superabsorbents have been placed among fibers to make absorbent pads which combine the cushioning properties and the integrity of fibrous pads with the liquid holding capacity of the superabsorbent. However, these combinations have been disappointing because the liquid holding capacity has fallen far short of the expected total for fibers and superabsorbent combined.

Perhaps these failures can be attributed to the fact that a particle of superabsorbent swells and in so doing pushes the fibers apart and occupies void space among the fibers. This void space now occupied by the superabsorbent could previously have been occupied by liquid.

The present invention provides optimum use of the superabsorbent effectiveness by confining the superabsorbent in a specially allocated space so that it does not occupy voids between the fibers.

SUMMARY OF THE INVENTION

According to the present invention, a catamenial device is provided comprising a moisture permeable outer layer containing a fibrous absorbent body including one or more discrete pockets therein, at least a portion of each of said pockets being moisture permeable, and each of said pockets containing therewithin a plurality of discrete particles of hydrocolloid material, said particles of hydrocolloid material being retained in spaced relationship relative to one another by discrete introfying particles disposed within each pocket.

Suitable pockets can be individual cells or strips of cells or in fact multiple cells in both length and width providing a type of "quilt". Each of the discrete cells contains a mixture of a superabsorbent and introfying particles.

The particulate absorbent materials contemplated herein contain water-insoluble but water-swellable polymeric substances having at least about 25% of their molecular structure composed of hydrophilic groups and capable of retaining water in an amount which is at least 10 times the weight of the absorbent material in dry form, and preferably about 15 to about 70 times the weight, or more.

Illustrative particulate absorbent materials that are suitable for the present purposes are powdered graft copolymers of a water-insoluble polysaccharide such as starch or cellulose having hydrophilic chains of carboxyl-, carboxylate-, and/or carbamide-bearing moieties.

Water-insoluble starch or a wide variety of cellulosic fibers can be utilized as starting materials for producing graft copolymers of this general type. Typical of such cellulosic fibers are: cotton, cotton linters, wood pulp, bagasse pulp, jute, rayon, and the like. The polysaccharide chains are then modified by grafting thereon a hydrophilic chain of the general formula

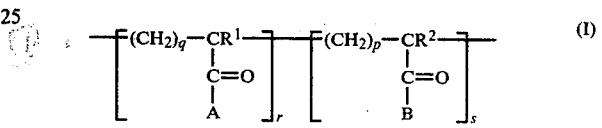

wherein A and B are selected from the group consisting of $-OR^3$, $-O$(alkali metal), $-OHNH_3$, $-NH_2$, wherein $R^1$, $R^2$ and $R^3$ are selected from the group consisting of hydrogen and alkyl having 1 to 4 carbon atoms, wherein r is an integer having a value of 0 to about 5000, s is an integer having a value of 0 to about 5000, r plus s is at least 500, p is an integer having a value of zero or 1, and q is an integer having a value of 1 to 4.

Preferred hydrophilic chains are hydrolyzed polyacrylonitrile chains and copolymers of polyacrylamide and sodium polyacrylate. In another preferred embodiment both ionizable polymeric moieties and non-ionizable polymeric moieties can be grafted on the same polysaccharide backbone.

While the detailed mechanism by which the grafting of the hydrophilic chain or chains onto a starch or a cellulosic backbone is not fully known, it is believed that grafting takes place through a free radical mechanism whereby the free radical is situated on the backbone which serves as a reducing agent, and the hydrophilic chain is attached to the starch or cellulosic reducing agent through a carbon linkage. The produced graft copolymer using a cellulosic backbone is of the type

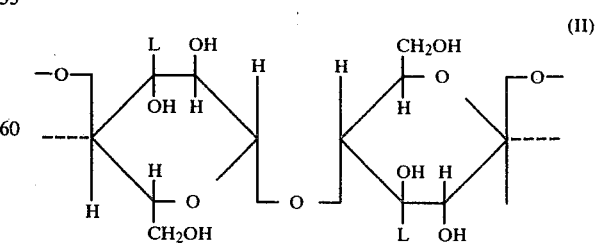

wherein L represents the hydrophilic chain of Formula I, above. The graft copolymer using a starch backbone is substantially similar to that represented by Formula I except that a starch backbone is present in lieu of a cellulosic backbone.

Also suitable as absorbents are cross-linked synthetic polymers and grafts on polysaccharides of synthetic polymers or synthetic copolymers.

A particulate material that is particularly well suited for the purposes of the present invention is Permasorb 10, a cross-linked synthetic polymer commercially available in the form of a powder from the National Starch and Chemical Corp.

The introfying particulate material is substantially inert mineral substances of a desirable particle size which enhance the impregnation of the superabsorbent with the liquid. In effect, the introfying material is a separator. In other words, it separates the hydrocolloid particles one from another. The introfying material is non-reactive, non-swellable, and crush resistant, and is a particulate material. Examples include particles of volcanic rock such as perlite, diatomaceous earth such as Celite, inorganic clay such as kaolin, and the like.

The material used to form the pockets is constructed, at least in part, of a permeable material. Typical liquid permeable materials are water-permeable paper, for example, high wet strength paper used for tea bags, non-woven fabrics, creped tissues, reticulated foam or screening, and the like. It is advantageous if the material is heat sealable for ease in formation of the pocket cell. If not, suitable adhesives or tape or other sealing means may be used. One suitable water-permeable paper is a product of the Dexter Corporation, Windsor Locks, Connecticut, identified as Grade 1234. It is a high quality, two phase teabag paper made from a blend of manila hemp and cellulose fibers in one phase and an integral layer of heat sealable thermoplastic fibers in the other phase.

The catamenial device of the present invention comprises a moisture permeable outer layer and an absorbent batt containing the pockets discussed above. Each pocket contains a substantially uniform admixture of hydrocolloid particulate material and introfying particles.

Several different types of outer layer materials may be used for the moisture permeable layer. For example, the outer layer may be made up of a mixture of fibers consisting predominantly of inexpensive short cellulosic fibers such as wood pulp fibers or cotton linters, in amounts of about 75% to about 98%, the balance being textile length fibers such as rayon as described in U.S. Pat. No. 3,633,348 to Liloia et al.

The outer layer may also be made of an apertured, non-woven fabric which is formed, for example, in accordance with the teachings of commonly assigned U.S. Pat. Nos. 2,862,251; 3,081,514 and 3,081,515. Briefly, such fabrics are foraminous structures wherein groups or groupings of fibers have been rearranged from a fibrous non-woven starting web into positions surrounds less dense fabric portions by passage of a fluid through the starting material. The fibers within the groupings are mechanically interlocked, and may be arranged into various patterns, as is well known by those skilled in the art. A suitable binder may be utilized to help retain the fibers in their rearranged locations, as is also well known by those skilled in the art. The fabric can be made of naturally occurring fibers, synthetic fibers, or blends thereof.

In addition, the outer layer can be formed of a nonapertured material, such as a non-woven isotropic web, or the like.

The highly moisture-absorbent fibrous pad or batt, which usually is substantially rectangular in shape but smaller than the facing sheet and the backing sheet, can be formed in accordance with the teachings of U.S. Pat. No. 3,612,055 to Mesek et al. If desired, a highly moisture-absorbent layer can be provided substantially coextensive with backing sheet and facing sheet.

The body of the batt is substantially more wettable than the outer layer and tends to draw liquid away from the outer layer. The individual fibers of the batt are extremely wettable, generally having liquid-fiber contact angles below about 15° and approaching zero in the optimum embodiment, as described in detail in the above-mentioned application. The wickability, or preferential absorptivity of the body of the batt for water is limited, however, by its low density which results in a large effective capillary radius for the capillaries between adjacent fibers.

The pressure causing a liquid to enter a cylindrical capillary is expressed by the equation:

$$P = 2\nu \cos \theta / \tau$$

wherein
P is the capillary pressure,
$\nu$ is the surface tension of the liquid,
$\theta$ is the liquid-fiber contact angle, and
r is the capillary radius.

With a given liquid, the pressure (capillary force) increases with the cosine of the liquid-fiber contact angle (reaching a maximum where the angle is zero), and decreases with narrower capillary radii so that narrower capillaries will draw liquid from wider ones.

The relative wickability between the outer layer and the body of the batt is affected by both the relative densities of the layers and the relative wettability of the individual fibers in each layer. The outer layer is sometimes more dense than the body of the batt, tending to provide greater wickability in the outer layer, but even then the individual fibers of the batt have substantially smaller liquid-fiber contact angles than those of the outer layer, overcoming the density difference and providing a substantial overall increase in capillary pressure to absorb liquid into the body of the batt.

In accordance with the present invention a substantially uniform admixture of a superabsorbent in particulate form and introfying particulate material are provided in one or more pockets in the absorbent batt of the catamenial device. The admixture is placed in the pockets in a portion such that when the superabsorbent swells there is adequate space in the enclosed pocket to retain the swollen substance. The pockets are placed in the absorbent batt. In a preferred embodiment, a section of the absorbent batt is cut out and the pocket or pockets of the admixture are placed in the cut-out space.

While the size of the introfying particles is not critical to the present invention, it is preferred that they be no larger than the hydrocolloid particles. And, for purposes of the present invention, the introfying particles need not be of uniform size or shape. However, it is important that the introfying particles be blended in a uniform admixture with the hydrocolloid particles, and that the admixture have a bulk volume that is substantially greater than the bulk volume of the hydrocolloid particles themselves. In this regard, it is preferred that the admixture have a bulk volume that is from about 4 to about 60 times as great as the bulk volume of the hydrocolloid particles therein, with the most preferred admixture-hydrocolloid range being from about 20 to about 50. Bulk volume ratios of the type contemplated herein not only provide the desired spacing for the hydrocolloid particles, but also provide room for expansion of the hydrocolloid particles when they are wetted to capacity. Bulk volumes of the particulate materials may be measured by placing the particulate material in a graduated cylinder and shaking or vibrating it until constant volume is obtained.

In a specific example, when Permasorb 10, mentioned above, is the hydrocolloid and Celite FC (a diatomaceous earth commercially available from Johns-Manville Corp.) is the introfying particle, an admixture of equal weights of the two materials produces a total bulk volume which is about 4.6 times the bulk volume of the hydrocolloid particles therein, and an increase of the weight proportion of the Celite FC particles to six times the weight of the hydrocolloid particles produces a total bulk volume which is about 23.8 times the bulk volume of the hydrocolloid particles therein.

With a preferred introfying particle, such as perlite, which has a bulk density less than about 0.05 g./ml., the increase in bulk volume is substantially greater. A mixture of 2 parts by weight of perlite per part of Permasorb 10 produces a bulk volume which is about 22.8 times the bulk volume of hydrocolloid particles therein; and a mixture of 5 parts by weight of perlite per part of Permasorb 10 produces a bulk volume which is about 49.1 times as great as the bulk volume of the hydrocolloid particles therein.

When hydrocolloid particles of the type contemplated herein are blended with introfying particles of the type set forth above in bulk volume ratios as described above, the introfying particles cooperate to maintain the hydrocolloid particles in spaced relationship thereby preserving the interstitial network between the hydrocolloid particles and permitting liquid to circulate through the void areas and contact the exposed surfaces of all of the hydrocolloid particles. The introfying particles prevent adjacent hydrocolloid particles from coalescing when they are wetted and begin to swell, thereby maximizing utilization of the large absorptive capacity of the hydrocolloid particles. And, since the admixture is confined within one or more discrete pockets in the absorbent layer of the absorbent product, the swelling hydrocolloid particles do not expand in the void areas in the adjacent fibrous portion of the absorbent layer so that the capillary network of the fibrous portion is not impaired.

The inventive concept of the present application has applicability to a wide variety of absorbent products illustrated in the accompanying drawings, in which.

DESCRIPTION OF ILLUSTRATED EMBODIMENTS

Figure 1:
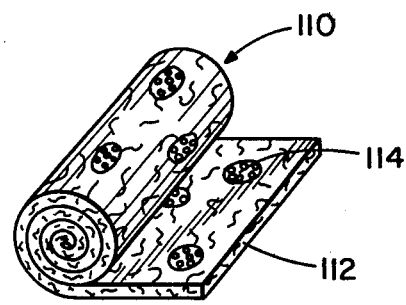
FIG. 1 is a perspective view of a partially rolled blank for compressing into a finished catamenial tampon embodying this invention.

While this invention is susceptible of embodiment in many different forms, there is shown in the drawings and will herein be described in detail preferred embodiments of the invention with the understanding that the present disclosure is to be considered as an exemplification of the principles of the invention and is not intended to limit the invention to the embodiments illustrated. The scope of the invention will be pointed out in the appended claims.

Figure 2:
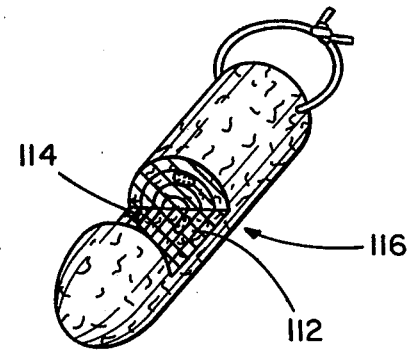
FIG. 2 is a perspective view of a finished tampon made from the blank of FIG. 1, a portion thereof being broken away to show interior detail.

Referring now to FIGS. 1 and 2, an embodiment of a catamenial tampon is illustrated. Typically the tampon is made up of absorbent particulate matter, most commonly of cellulosic fibers. The fibers are formed into a loose, generally rectangular pad. A withdrawal string is disposed around the pad and then the pad is wound or folded into the form of a blank which is then compressed in a die into the final tampon shape.

Figure 2A:
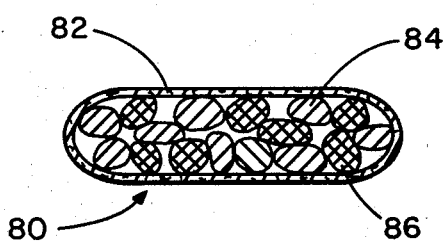
FIG. 2A is an enlarged cross-sectional view through one of the discrete pockets of the present invention containing a uniform admixture of hydrocolloid and introfying particles.

Shown in FIG. 1 is an elongated pad 112 of absorbent material having a generally rectangular shape and illustrated as formed into a cylinder 110 by rolling from one end to the other in a direction parallel to the longitudinal sides of the pad. In accordance with this aspect of the invention, pockets 114 are imbedded in the pad 112 prior to rolling into a cylinder. The pockets 114 (80 in FIG. 2A) are a permeable membrane 82 surrounding hydrocolloid particles 84 and introfying particles 86 as shown in FIG. 2A.

FIG. 2 illustrates the shaped tampon 116 prepared from the cylinder blank 110 of FIG. 1. The fragmentary view shows the pockets 114 and the absorbent pad 112 as layers.

Figure 3:
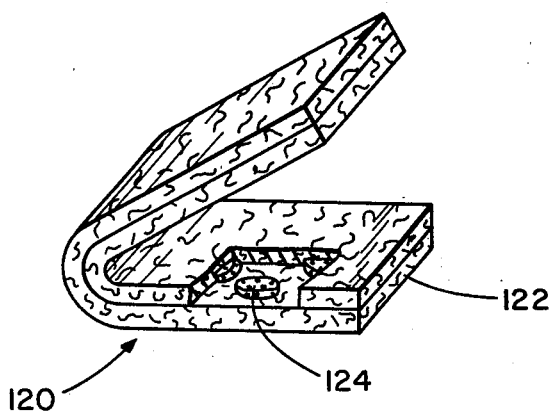
FIG. 3 is a perspective view of a partially folded blank for compressing into a second catamenial tampon of the present invention.
Figure 4:
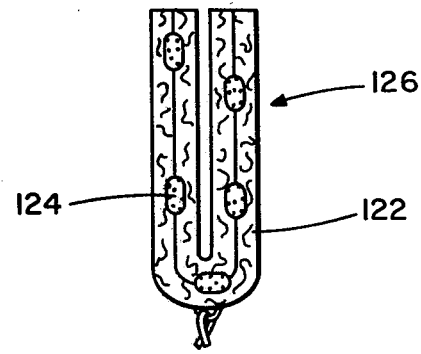
FIG. 4 is a cross-sectional view of the finished tampon made from the blank of FIG. 3 taken through an axial plane through the tampon.

FIGS. 3 and 4 depict another tampon 126 shaped from a multilayer pad 120 formed by folding over a single layer 122 of absorbent batt. In this instance the pockets 124 are placed so as to lie between the layers and project into each layer. The pad 120 is then formed into the tampon 126 of FIG. 4 by compression.

Figure 5:
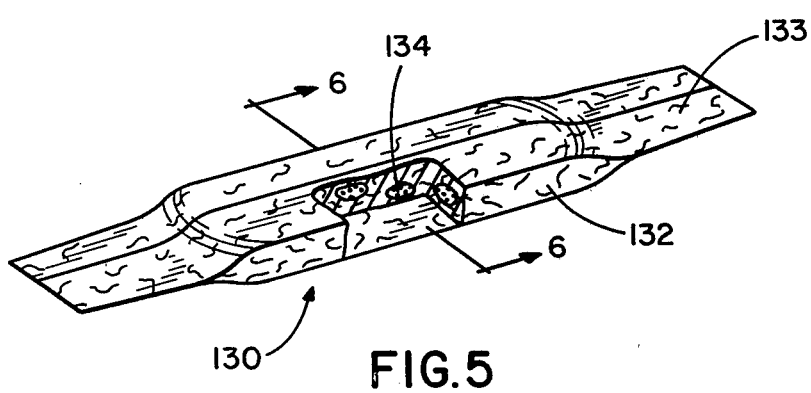
FIG. 5 is a perspective view of a catamenial sanitary napkin embodying this invention, a portion thereof being broken away to show interior detail.
Figure 6:
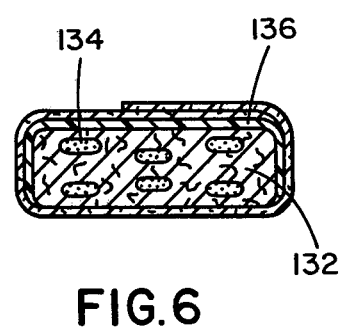
FIG. 6 is a cross-sectional view of the sanitary napkin of FIG. 5 taken along line 6—6.

Referring now to FIGS. 5 and 6 another embodiment, specifically a sanitary napkin, is illustrated. An absorbent pad 132 comprised of, for example, wood pulp, is enveloped by a liquid permeable wrapper 133 which extends at both ends beyond the pad so as to provide attachment tabs. A liquid impermeable sheet 136 is sandwiched on one surface of the pad, between the pad and the wrapper, and may extend, at least partially, over the sides of the pad. The impermeable sheet 136 may be, for example, a polyethylene film. Throughout the pad 132 there are distributed pockets 134 containing the superabsorbent and introfying particles surrounded by a moisture permeable membrane. In accordance with the present invention, the hydrocolloid particles are dry, solid granules when the catamenial device is manufactured, having been ground or otherwise formed to maximize the exposed surface area of the hydrocolloid material. The hydrocolloid particles need not have the same size or shape, or chemical composition since the present invention contemplates that blends of chemically different hydrocolloidal materials may be utilized. However, as presently understood, it is desired that the hydrocolloid particles be chemically identical, and generally of the same size and shape.

The introfying particles are physically separate from and not chemically or otherwise bound or joined to the hydrocolloid particles. The introfying particles are dry, solid granules that are blended and distributed in a uniform admixture with the hydrocolloid particles, and are present in sufficient quantity to segregate and separate the hydrocolloid particles from one another, even when the hydrocolloid particles swell and expand upon being wetted. The introfying particles contemplated by the present invention such as perlite and Celite mentioned above, have sufficient structural integrity to substantially retain their size and shape when subjected to compressive forces exerted by the swelling and expanding hydrocolloid particles. And, since the bulk volume of the admixture is substantially greater than the bulk volume of the hydrocolloid particles, the introfying particles function to preserve the interstices around the hydrocolloid particles thereby insuring liquid impinging upon the pockets 22 will have access to all of the hydrocolloid particles therein.

Referring to FIG. 2A each pocket 80 is illustrated as being formed by a pair of sheet-like membranes 82. Membranes 82 are moisture pervious members having a pore size sufficient to permit entry of liquid, but small enough to prevent the hydrocolloid particles and introfying particles from escaping. Illustratively the membranes 82 may be formed of the high wet strength, inherently heat-sealable Dexter tea bag paper mentioned, and such membranes may be heat sealed to one another around their perimeter. The present invention also contemplates the utilization of bags and pouches which may, for example, be formed by folding a single moisture permeable membrane upon itself and sealing facing surfaces together to form a closed cell or pocket.

While the embodiment of FIGS. 1-6 shows the pockets 80 as being spaced from one another, the present invention also contemplates the provision of a plurality of connected, yet independent and non-communicating pockets.

As is set forth above, each of the pockets associated with the absorbent structures contemplated herein contains a uniform admixture of discrete hydrocolloid particles and introfying particles, with the particles of the admixture being present in a bulk volume range of from about 4 to about 60 times the bulk volume of the hydrocolloid particles themselves; and with the particles of the admixture preferably being present in a bulk volume range of from about 20 to about 50 times the bulk volume of the hydrocolloid particles themselves. In each of the disclosed arrangements, the hydrocolloid and introfying particles occupy only a portion of the internal volume of the individual pocket, so that the hydrocolloid particles can expand without rupturing the walls of the individual pockets. The present invention also contemplates that the walls or membranes of the individual pockets may be capable of expansion, such as by pleating or creping the materials from which the pockets are formed.

With pockets of the type described above, when the hydrocolloid particles are wetted and begin to swell, they expand to substantially fill the internal volume of the individual pockets, after which the individual pockets themselves may expand. The expanding walls will push the adjacent fibers of the batt aside, but the swelling hydrocolloid particles will remain trapped within the pockets and will not occupy the capillary voids of the fibrous panel. As a result the total absorptive capacity of the structure is significantly increased. Since the unique pocket arrangement of the present invention significantly improves the total absorptive capacity of the structure, a lesser amount of fibrous material may be used for a tampon or napkin of a given desired absorptive capacity, with the result that the tampon or napkin is less bulky and more comfortable to the wearer.

While the present invention has been described in detail with respect to certain absorbent structures, the present invention should be considered as being applicable to absorbent articles generally, unless indicated to the contrary in the appended claims.

I claim:

1. A catamenial device comprising a moisture permeable outer layer containing an absorbent layer, said absorbent layer including at least one discrete pocket therein, at least a portion of said pocket being moisture permeable, said pocket containing therewithin a uniform admixture of discrete particulate hydrocolloid material and discrete introfying particles which maintain the particles of hydrocolloid material in spaced relationship relative to one another.

2. A catamenial device as set forth in claim 1 where said absorbent layer includes a plurality of discrete pockets each containing an admixture of hydrocolloid and introfying particles.

3. A catamenial device as set forth in claim 2 wherein said absorbent layer includes a cellulosic fibrous batt of loosely compacted fibers adjacent to said pockets.

4. A catamenial device as set forth in claim 1 wherein said device is a tampon.

5. A catamenial device as set forth in claim 1 wherein said device is a sanitary napkin.

6. A sanitary napkin comprising a moisture permeable outer layer, and an absorbent batt surrounded by said outer layer, said absorbent batt being a cellulosic fibrous batt of loosely compacted fibers and including a plurality of discrete pockets therein, at least a portion of each of said pockets being moisture permeable, and each of said pockets containing therewithin a uniform admixture of discrete particles of hydrocolloid material, said particles of hydrocolloid material being retained in spaced relationship relative to one another by discrete introfying particles disposed within each pocket.

7. A sanitary napkin as set forth in claim 6 wherein said pockets are spaced from one another.

8. A sanitary napkin as set forth in claim 6 wherein said pockets are interconnected.

9. A sanitary napkin as set forth in claim 6 wherein each pocket includes a moisture permeable membrane surrounding said hydrocolloid and introfying particles.

10. A tampon comprising a moisture permeable outer layer, and an absorbent batt surrounded by said outer layer, said absorbent batt being a cellulosic fibrous batt of loosely compacted fibers and including a plurality of discrete pockets therein, at least a portion of each of said pockets being moisture permeable, and each of said pockets containing therewithin a uniform admixture of discrete particles of hydrocolloid material, said particles of hydrocolloid material being retained in spaced relationship relative to one another by discrete introfying particles disposed within each pocket.

11. A tampon as set forth in claim 10 wherein said pockets are spaced from one another.

12. A tampon as set forth in claim 10 wherein said pockets are interconnected.

13. A tampon as set forth in claim 10 wherein each pocket includes a moisture permeable membrane surrounding said hydrocolloid and introfying particles.

14. A catamenial device comprising a moisture permeable outer layer, containing an absorbent batt, said absorbent batt including at least one discrete pocket therein, at least a portion of said pocket being moisture permeable, and said pocket containing therewithin a plurality of discrete particles of hydrocolloid material, said particles of hydrocolloid material being retained in spaced relationship relative to one another by discrete introfying particles disposed within said pocket, said hydrocolloid particles and said introfying particles being present in said pocket in a uniform admixture which has a bulk volume from about 4 to about 60 times a great as the bulk volume of the hydrocolloid particles therein.

15. A catamenial device as set forth in claim 14 wherein the device is a sanitary napkin.

16. A catamenial device as set forth in claim 14 wherein the device is a tampon.

17. A catamenial device comprising a moisture permeable outer layer containing an absorbent batt, said absorbent batt including at least one discrete pocket therein, at least a portion of said pocket being moisture permeable, and said pocket containing therewithin a plurality of discrete particles of hydrocolloid material, said particles of hydrocolloid material being retained in spaced relationship relative to one another by discrete introfying particles disposed within said pocket, said introfying particles having sufficient structural integrity to substantially retain their size and shape under compressive forces exerted by said hydrocolloid particles as they swell and expand when wetted, said hydrocolloid particles and said introfying particles being present in said pocket in a uniform admixture which has a bulk volume from about 4 to about 60 times as great as the bulk volume of the hydrocolloid particles therein.

18. A catamenial device as set forth in claim 17 wherein said hydrocolloid and introfying particles occupy only a portion of the internal volume of said pocket.

19. A catamenial device as set forth in claim 17 wherein at least a portion of said pocket is defined by an expansible membrane.

20. A catamenial device as set forth in claim 17 wherein said pocket is formed by a bag formed of a porous, high wet strength, light-weight filter paper.

21. A catamenial device as set forth in claim 20 wherein said bag is formed of two sheets of filter paper secured to one another around their periphery.

22. A catamenial device as set forth in claim 17 wherein said introfying particles have a bulk density less than about 0.05 g./ml.

23. A catamenial device as set forth in claim 17 wherein said bulk volume of said uniform admixture is from about 20 to about 50 times the bulk volume of the hydrocolloid particles therein.

* * * * *